United States Patent
Møller

(10) Patent No.: US 9,956,351 B2
(45) Date of Patent: May 1, 2018

(54) INJECTION DEVICE WITHOUT A GEARING

(75) Inventor: Claus Schmidt Møller, Fredensborg (DK)

(73) Assignee: Becton, Dickinson and Company, Franklin Lakes, NJ (US)

( * ) Notice: Subject to any disclaimer, the term of this patent is extended or adjusted under 35 U.S.C. 154(b) by 188 days.

(21) Appl. No.: 13/510,318

(22) PCT Filed: Nov. 19, 2010

(86) PCT No.: PCT/DK2010/000151
§ 371 (c)(1),
(2), (4) Date: Jul. 17, 2012

(87) PCT Pub. No.: WO2011/060785
PCT Pub. Date: May 26, 2011

(65) Prior Publication Data
US 2012/0277683 A1 Nov. 1, 2012

(30) Foreign Application Priority Data
Nov. 20, 2009 (DK) .................. 2009 01228

(51) Int. Cl.
*A61M 5/31* (2006.01)
*A61M 5/315* (2006.01)
*A61M 5/24* (2006.01)

(52) U.S. Cl.
CPC .... *A61M 5/31573* (2013.01); *A61M 5/31551* (2013.01); *A61M 5/31585* (2013.01);
(Continued)

(58) Field of Classification Search
CPC ................ A61M 5/24; A61M 5/31525; A61M 5/31553; A61M 5/31535; A61M 5/3158;
(Continued)

(56) References Cited

U.S. PATENT DOCUMENTS 5,017,190 A 5/1991 Simon et al.
5,104,380 A 4/1992 Holman et al.
(Continued)

FOREIGN PATENT DOCUMENTS

CN 101068586 A 11/2007
EP 0327910 A2 8/1989
(Continued)

OTHER PUBLICATIONS

Chinese Office Action issued in Chinese Patent Application No. 201080052413.4 dated Sep. 6, 2013.
(Continued)

*Primary Examiner* — Bhisma Mehta
*Assistant Examiner* — William Frehe
(74) *Attorney, Agent, or Firm* — Dickinson Wright PLLC

(57) ABSTRACT

A dose delivery device is disclosed wherein a dose can be set by rotating a dose setting member, whereby a push button (4) is elevated from one end of the device a distance proportional to the set dose from a position fixed relative to the housing, and wherein the set dose can then be injected by pressing the push button back to its non-elevated position, through which motion a piston rod will move approximately the same distance. The invention provides a method of forcing a numbered scale drum to rotate both during dose setting and injection to allow the user to read the remaining dose at any time during setting and injecting a dose.

20 Claims, 10 Drawing Sheets

(52) U.S. Cl.
CPC ....... *A61M 5/24* (2013.01); *A61M 2005/2407* (2013.01); *A61M 2005/3125* (2013.01); *A61M 2005/3126* (2013.01); *A61M 2205/581* (2013.01); *A61M 2205/582* (2013.01)

(58) Field of Classification Search
CPC ............ A61M 5/3156; A61M 5/31593; A61M 5/31563; A61M 5/31581; A61M 5/31595; A61M 5/31551; A61M 5/31555; A61M 5/31591; A61M 5/31561
USPC .......................................... 604/207–211, 189
See application file for complete search history.

(56) References Cited

U.S. PATENT DOCUMENTS

| | | | |
|---|---|---|---|
| 5,114,406 | A | 5/1992 | Gabriel et al. |
| 5,226,895 | A | 7/1993 | Harris |
| 5,232,459 | A | 8/1993 | Hjertman |
| 5,271,527 | A | 12/1993 | Haber et al. |
| 5,304,152 | A | 4/1994 | Sams |
| 5,308,340 | A | 5/1994 | Harris |
| 5,383,865 | A | 1/1995 | Michel |
| 5,391,157 | A | 2/1995 | Harris et al. |
| 5,501,670 | A | 3/1996 | Sak |
| 5,591,136 | A | 1/1997 | Gabriel |
| 5,626,566 | A | 5/1997 | Petersen et al. |
| 5,938,642 | A | 8/1999 | Burroughs et al. |
| 5,984,900 | A | 11/1999 | Mikkelsen |
| 6,001,089 | A | 12/1999 | Burroughs et al. |
| 6,004,297 | A | 12/1999 | Steenfeldt-Jensen et al. |
| 6,086,567 | A | 7/2000 | Kirchofer et al. |
| 6,106,501 | A | 8/2000 | Michel |
| 6,221,046 | B1 | 4/2001 | Burroughs et al. |
| 6,235,004 | B1 | 5/2001 | Steenfeldt-Jensen et al. |
| 6,569,126 | B1 | 5/2003 | Poulsen et al. |
| 6,582,404 | B1 | 6/2003 | Klitgaard et al. |
| 6,663,602 | B2 | 12/2003 | Moller |
| 6,786,890 | B2 | 9/2004 | Preuthun et al. |
| 6,899,698 | B2 | 5/2005 | Sams |
| 6,899,699 | B2 | 5/2005 | Enggaard |
| 6,945,961 | B2 | 9/2005 | Miller et al. |
| 7,094,221 | B2 | 8/2006 | Veasey et al. |
| 7,104,972 | B2 | 9/2006 | Moller et al. |
| 7,112,187 | B2 | 9/2006 | Karlsson |
| 7,118,553 | B2 | 10/2006 | Scherer |
| 7,195,616 | B2 | 3/2007 | Diller et al. |
| 7,241,278 | B2 | 7/2007 | Moiler |
| 7,291,132 | B2 | 11/2007 | DeRuntz et al. |
| 7,361,161 | B2 | 4/2008 | Bainton |
| 7,427,275 | B2 | 9/2008 | DeRuntz et al. |
| 7,445,613 | B2 | 11/2008 | Hommann |
| 7,500,966 | B2 | 3/2009 | Hommann |
| 7,517,334 | B2 | 4/2009 | Jacobs et al. |
| 7,553,299 | B2 | 6/2009 | Veasey et al. |
| 7,850,662 | B2 | 12/2010 | Veasey et al. |
| 7,905,867 | B2 | 3/2011 | Veasey et al. |
| 7,935,088 | B2 | 5/2011 | Veasey et al. |
| 8,021,345 | B2 | 9/2011 | Veasey et al. |
| 2004/0097883 | A1 | 5/2004 | Roe |
| 2005/0165363 | A1* | 7/2005 | Judson .................... A61M 5/24 604/209 |
| 2006/0184117 | A1* | 8/2006 | Knight .................... A61M 5/24 604/135 |
| 2008/0183139 | A1 | 7/2008 | Burren et al. |
| 2008/0243087 | A1 | 10/2008 | Enggaard et al. |
| 2009/0012479 | A1 | 1/2009 | Moller et al. |
| 2009/0264828 | A1 | 10/2009 | Dette et al. |
| 2009/0275916 | A1 | 11/2009 | Harms et al. |
| 2009/0293870 | A1 | 12/2009 | Brunnberg et al. |
| 2009/0299297 | A1 | 12/2009 | Moller et al. |
| 2010/0094205 | A1 | 4/2010 | Boyd et al. |
| 2010/0114037 | A1 | 5/2010 | Moser et al. |
| 2010/0145282 | A1 | 6/2010 | Hansen et al. |
| 2010/0152671 | A1 | 6/2010 | Raab et al. |
| 2010/0179485 | A1 | 7/2010 | Radmer et al. |
| 2010/0324493 | A1 | 12/2010 | Plumptre |
| 2011/0028911 | A1 | 2/2011 | Veasey et al. |
| 2011/0034902 | A1 | 2/2011 | Markussen |
| 2011/0046567 | A1 | 2/2011 | Radmer et al. |

FOREIGN PATENT DOCUMENTS

| | | | |
|---|---|---|---|
| EP | 1923085 A1 | 5/2008 | |
| EP | 1603610 A1 | 9/2008 | |
| EP | 2221077 A2 | 8/2010 | |
| WO | 9938554 A1 | 8/1999 | |
| WO | 03/080160 A1 | 10/2003 | |
| WO | 2004078242 A2 | 9/2004 | |
| WO | 2005018721 A1 | 3/2005 | |
| WO | 2006/058883 A2 | 6/2006 | |
| WO | WO 2006058883 A2 * | 6/2006 | ........ A61M 5/31551 |
| WO | 2006058883 A2 | 7/2006 | |
| WO | 2006/084876 A1 | 8/2006 | |
| WO | WO 2006058883 A3 * | 9/2006 | ........ A61M 5/31545 |
| WO | 2007/107431 A1 | 9/2007 | |
| WO | 2007107431 A1 | 9/2007 | |
| WO | 2008058667 A | 5/2008 | |
| WO | 2009039851 A1 | 4/2009 | |
| WO | WO 2010/139691 | 12/2010 | |

OTHER PUBLICATIONS

International Search Report: International Application No. PCT/DK2010/000151; International Application Filing Date Nov. 19, 2010; dated Apr. 7, 2011.

Notice of Reason for Rejection, Issued in Patent Application No. 2012-539183, dated Aug. 21, 2014, Applicant—Yuzuru Okabe et al., 5 pages incl. Eng. Translation.

* cited by examiner

INJECTION DEVICE WITHOUT A GEARING

TECHNICAL FIELD

The invention relates to a dose delivery device, wherein a dose can be set by rotating a dose setting member, whereby a push button is elevated from one end of the device, and the set dose can then be injected by pressing the push button back to its non-elevated position, thereby moving a piston rod co-operating with the piston in a cartridge and expelling a medicament out of the cartridge through a needle.

BRIEF DISCUSSION OF RELATED ART

From EP 0 327 910 is known an injection device in which a dose is set in the classic way by rotating a tubular injection button engaging a threaded piston rod, thereby causing the injection button to elevate from the end of the injection device. By pressing down the injection button until abutment with a fixed stop, the threaded piston rod is moved a distance corresponding to the movement of the injection button. The piston rod mates a piston in a cartridge and medicine is expelled from the cartridge. This kind of injection device transmits the injection force directly to the piston of the cartridge but provides no gearing, i.e. the linear movement of the injection button corresponds exactly to the linear movement of the piston rod.

However, the above described device does not comprise a numbered scale drum, and the amount of a set dose has to be calculated by adding a one digit scale with a ten digit scale. As all parts of the dose setting mechanism are reset by linear movements when a set dose is injected, the increment size of a unit in the dose setting mechanism is very small, and a dose can only be set to every second unit.

EP 1 003 581 describes a number of methods to achieve a dose setting providing a gearing between the axial movement of the piston rod and the dose setting member to allow a scale drum with sufficient space for numbers to be added. In one embodiment a dose setting member is rotated in a thread in the housing having a higher pitch than the pitch on the piston rod. When pressure is added to an injection button, the piston rod is being rotationally coupled to the dose setting member and as the piston rod is rotated in a nut fixed to the housing it is moved forward until the dose setting member abuts a fixed stop. This embodiment provides a gearing in movement, but does not reduce the needed injection force, as the transmission from linear movement to rotational movement and back from rotational to linear movement eats up most of the obtained force reduction due to friction.

The unit increment size in the dose setting mechanism for above mentioned embodiments is rather big and plenty of space for numbers are provided. However, for people with small hands and fingers it might be a problem to inject a set dose without changing the grip during injection due to the long movement of the pushbutton, especially if a user wants to use the index finger for injection In WO 2008/058667 a piston rod is provided with a first thread which is engaging a driver and a second thread handed in the opposite direction which is engaging the housing. A numbered scale drum is rotating together with the driver when setting a dose and is decoupled from the driver, when the dose is injected. When a dose is set the driver is rotated up along the piston rod in a helical movement, due to the coupling with the scale drum, and the piston rod is thereby prevented from rotating in the dose setting situation. When the dose is injected, the driver, which is now prevented from rotating, is pressed down and consequently it is pushing the piston rod forward. As the piston rod is also engaged with the housing in an opposite handed thread, it will rotate and thereby move a shorter distance than the driver.

WO 2005/018721 describes a pen with a gearing mechanism based on two threads handed in the same direction and a third thread on the piston rod which is not directly a part of the gearing mechanism. A piston rod is connected with a nut. A non-rotational driver is engaging a scale drum via a first thread and the nut via a second thread. The pitch of the first thread is bigger than the pitch of the second pitch and the difference between them is equal to the pitch of the piston rod. When a dose is set, the nut is rotationally locked to the scale drum, and is thereby rotated and elevated a distance corresponding to the elevation of the driver. When the set dose is to be injected, the nut disengages the scale drum to engage the non-rotational driver. As the scale drum is pushed into the device, the rotation of the scale drum will cause the non-rotational driver to retract into the scale drum and the resulting displacement of the driver to be equal to the set dose. The nut is now pushed back to zero position bringing the piston rod along causing insulin to be expelled. It should be noted however that the pitches of the threads are dependent of number of increments per revolution and unit size etc. and the dose force will be relatively high due to the low driving pitch.

In WO 2009/039851 a gearing nut is provided with a first thread which is engaging a driver and a second thread handed in the opposite direction which is engaging the housing and is axially locked to a dosing nut. A dosing nut is engaged with a non-rotating piston rod in a thread connection. The driver and the housing are relatively locked against rotation. A numbered scale drum is rotating together with a dose setting grip when setting a dose and is decoupled from the dose setting grip, when the dose is injected. When a dose is set the dosing nut is rotated one distance up along the piston rod in a helical movement and the driver is pushed another distance by the scale drum. When the dose is injected, the non-rotating driver is pressed down via the dose setting grip and the relative axial and non-rotating movement between the driver and the housing will cause the gearing nut to move a shorter distance due to the two opposite handed threads. As the gearing nut is axially locked to the dosing nut, the dosing nut will be pressed down the same distance. The dosing nut is prevented from rotating during injection and it will therefore bring along the non-rotating piston rod.

The three above mentioned devices provides a smaller push-button movement per unit, but for users taking large doses and having small hands, it might still be a challenge to carry out an injection. At the same time they comprise additional parts to provide a gearing.

The invention provides an injection device comprising a numbered scale drum, a few and simple parts and with a short movement of the injection button during injection.

BRIEF SUMMARY

The invention relates to a dose delivery device comprising a housing, a dose selector, a push-button, a piston rod not rotating during dose setting and rotating during injection, a driver threadedly engaged with the piston rod and a numbered scale drum rotationally locked to the driver, wherein a dose can be set by rotating the dose selector, whereby the push-button is elevated from one end of the device a distance proportional to the set dose from a position fixed relative to the housing, and wherein the set dose can then be injected by pressing the push-button back to its non-elevated position, through which motion of the push-button the piston rod will move the same distance, characterised by the driver is rotated an angle in one direction when setting the dose, and together with the piston rod the same angle in the opposite direction when injecting the set dose.

By letting the driver rotate one way during dose setting and the other way together with the scale drum during injection, it is possible to rotate a numbered scale drum in such a way, that it will display the amount of a set or remaining dose correctly in any situation.

In an embodiment of the invention, the dose setting member and the push-button is formed as one integral part. Hereby it is achieved that the number of parts and, thus, the complexity and production costs of the device are reduced.

In another embodiment of the invention a numbered scale drum displaying the amount of a set dose is rotationally locked to the driver and axially locked to the push-button. Hereby a scale drum without any thread engagements with other parts causing loss of energy is provided.

In a further embodiment of the invention a numbered barrel is engaging a first thread in the housing having a first pitch and a second thread on the driver having a second pitch the second pitch being higher than the first pitch. In this way it is possible to let the numbered barrel rotate a bigger angle than the driver and at the same time to elevate more than the driver, and thereby it is possible to print bigger numbers and increase readability.

In a further embodiment of the invention a ratchet arm is provided on the numbered scale drum and wherein the ratchet arm cooperates with a protrusion in the housing in such a way, that when a dose is injected and the push-button is moved the initial distance the ratchet arm will pass over the protrusion in end of the injection, but when the pressure is removed from the push-button and the push-button is no longer moved the initial distance, the ratchet arm can pass the protrusion in the housing and a new dose can be set. This makes it more clear for the user when the injection is fulfilled.

In a further embodiment of the invention, the dose selector is rotationally coupled to the driver during dose setting and decoupled during injection. This has the advantage, that the dose selector does not rotate during injection and a separate pushbutton can be avoided.

In a further embodiment of the invention, the dose selector is indexed on certain positions on a revolution in the housing producing a clicking and tactile feed-back due to an interaction between the dose selector and the housing. In this way a separate item for producing a clicking sound is avoided and the dose-selector is prevented from rotating during dose injection.

In an even further embodiment of the invention a ratchet is provided between the dose selector and the driver to cause the dose selector to rotationally bring along the driver when a dose is set. This makes it unnecessary to couple and decouple the dose selector from the driver, as the torque produced in the thread engagement between the piston rod and the housing when injecting a dose will overcome the torque from the ratchet, and therefore the driver will rotate relative to the dose selector as the dose selector is prevented from rotating due to the dose setting clicks.

In yet another embodiment of the invention, the dose delivery device comprises a one-way ratchet which is rotational coupled to the piston rod. This has the function that it together with the friction in the piston helps preventing the piston rod from moving when a dose is set and at the same time it produces a clicking sound when injecting the dose.

In yet another embodiment of the invention, the dose delivery device comprises an item which is rotational coupled to the piston rod and which is rotational coupled to the housing during dose setting and decoupled during injection. This has the advantage that it in a more rigid way prevents the piston rod from moving when a dose is set.

In a further embodiment of the invention, the numbered scale drum moves axially together with the push-button and the scale drum couples rotationally to the ratchet when the push-button is pushed. This provides a very simple way to make the driver, the scale drum, the piston rod and the ratchet to rotate together when the dose is injected.

In yet another embodiment of the invention, the dose delivery device further comprises a non-rotationally window which is axially movable and which is engaged with the scale drum via a thread in such a way, that it moves axially in the opposite direction of the driver when setting and injecting a dose. This makes it possible to use a bigger area of the scale drum for the numbers and thereby to make the numbers bigger.

In yet another embodiment of the invention, a magnifier which enlarges the displayed number corresponding to the set dose is provided. In this way the readability and thereby the convenience in using the device is enhanced.

The invention provides a dose delivery device comprising a threaded piston rod engaged with a thread in an opening in a housing and engaged with a thread on a driver. A unidirectional ratchet is rotational locked to the piston rod and is axial but not rotational coupled to the driver. To set a dose the driver is rotated up along the piston rod in the locking direction of the ratchet. To correct a set dose, the driver is rotated back and the resistance in the ratchet prevents the ratchet and the piston rod from rotating. To inject the set dose the driver is coupled rotationally to the ratchet via a scale drum and pushed forward toward the needle end (this will be explained further). This will force the piston rod and the ratchet and the driver to rotate due to the thread engagement with the housing, and the resistance in the ratchet will be overruled and the ratchet will produce a clicking sound when the piston rod moves forward.

The dose delivery device is of the gearless kind where the movement of the pushbutton corresponds to the movement of the piston rod, which has the advantage that users having small fingers doesn't have to change grip during injection, and that injection using the index finger is possible. To display the amount of a set dose, a numbered scale drum is provided, which is rotational locked to the driver. The scale drum will display the amount of a set dose in a window in the housing. The scale drum is capable of moving axial a small distance relative to the driver. A dose selector is releasable coupled to the driver and is axial mating the scale drum via a gliding bearing. When the set dose is to be injected the dose selector which also acts as push-button is pushed a little forward which will disconnect it from the driver, and at the same time the scale drum is pushed a little forward which will lock the scale drum rotational to the ratchet. In this way a package comprising the piston rod, the driver, the scale drum and the ratchet are locked together rotationally. Further push on the push-button/dose selector will cause the package to rotate and move forward due to the thread connection between the housing and the piston rod. A spring between the scale drum and the driver will push the dose selector back in engagement with the driver after ending or interrupting the injection, and the scale drum and the ratchet will at the same time be disengaged.

The dose selector also acts as a bidirectional ratchet against the housing, to provide increments of a specified size around the length axis of the device and to provide a tactile and audible feed back. When the dose is injected, the dose selector does not rotate. However, an unintentional rotation during injection will cause no harm, as the dose selector and the driver are decoupled.

A window can be added to the housing to protect the user from touching the scale drum or a magnifier can be added to more clearly display the amount of a set dose. A window or a magnifier can also act as a stop for the maximum settable dose by having an inward reaching protrusion cooperating with the scale drum or another part of the device.

In another embodiment the scale drum has an outer thread having a pitch of e.g. the double of the pitch of the piston rod. A window item which might also comprise a magnifier and which is axial but not rotational movable relative to the housing is engaging the thread of the scale drum. When the scale drum rotates up along the piston rod, the window item moves down a bigger distance, and in that way more space on the scale drum is available for displaying numbers. A prolonged hole in the housing should allow the window item to display the number in different positions.

It should be noted, that the dose delivery device can be designed to be either disposable or rechargeable and to contain one, two or multiple cartridges at the time. If the dose delivery device is designed to be rechargeable, the piston rod must be able to rotate when the cartridge holder is disconnected.

BRIEF DESCRIPTION OF THE DRAWINGS

In the following the invention is described in further details with reference to the drawings, wherein.

DETAILED DESCRIPTION

Figure 1:
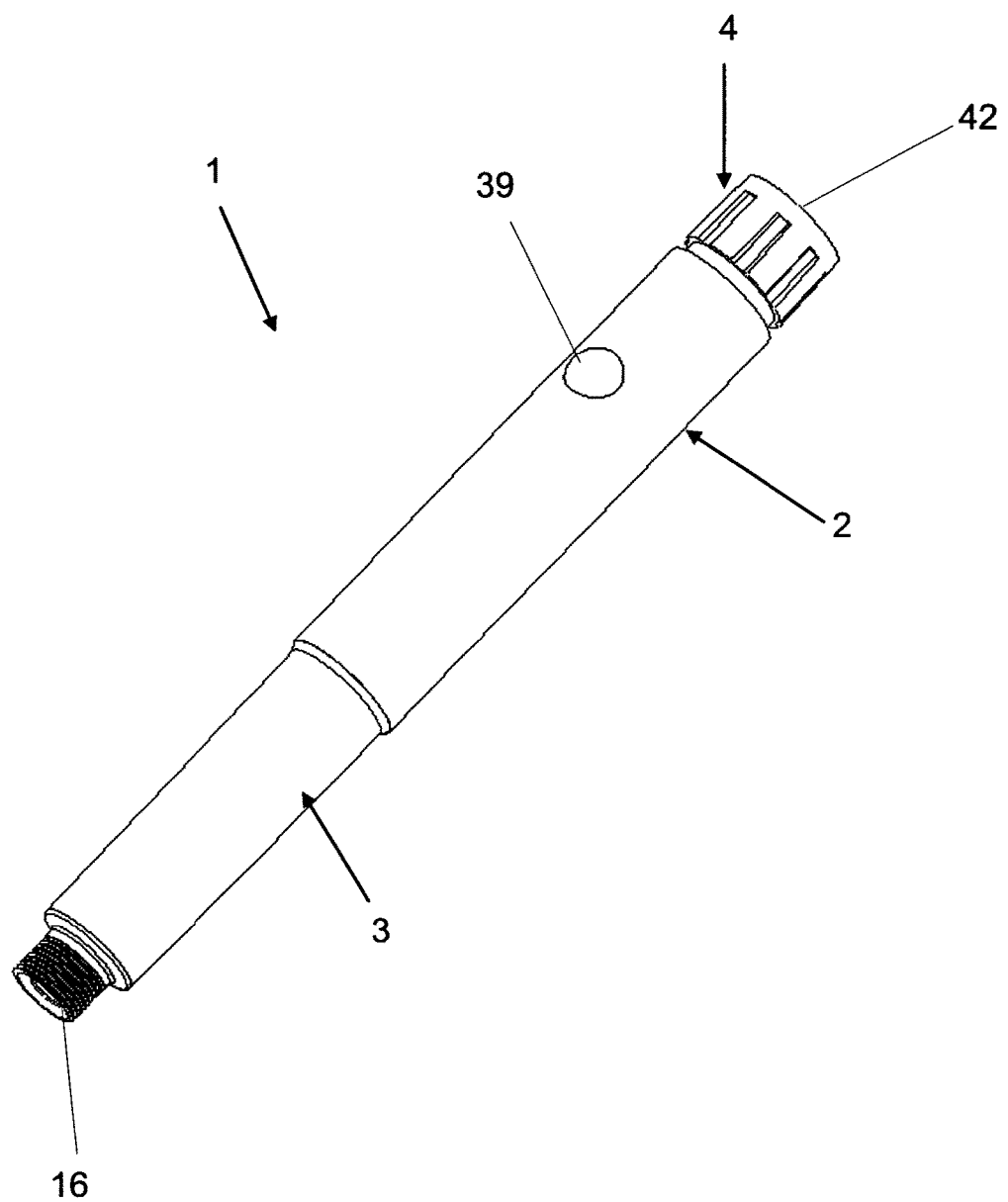
FIG. 1 shows a perspective view of a device according to the invention.
Figure 2:
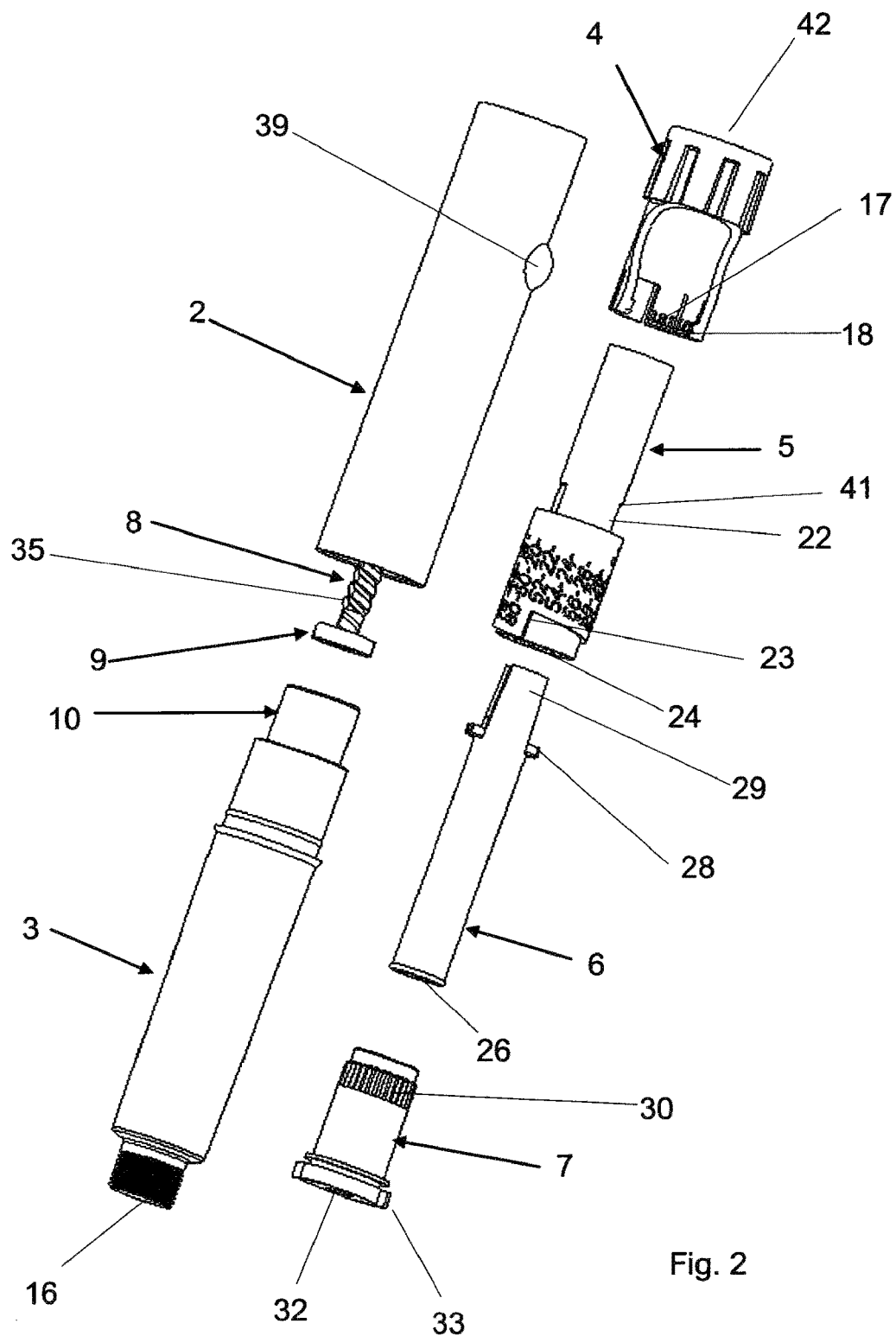
FIG. 2 shows an exploded view of a device according to the invention.

FIG. 1 shows a device 1 according to the invention in an oblique view. Visible is the housing 2 comprising a window 39, where the amount of a set dose can be displayed, the dose selector 4 by which a dose is set and injected and the cartridge holder 3 comprising a thread 16 for the attachment of a double-ended needle. The cartridge holder 3 also contains the medicine-filled cartridge 10 (visible in FIG. 2). The cartridge 10 comprises a piston, which cooperates with the piston rod 7 (visible in FIG. 4) of the injection system to expel a set dose of medicine from the cartridge 10 out through the needle. The cooperation between the different elements of the device 1 will be described in the following.

The dose selector of the shown embodiments is to be comprehended as an element by which a dose can be both set and injected. In other embodiments of the invention, the functions of the dose selector 4 could be divided into two elements—a dose setting button and an injection button.

The dose delivery device according to the invention has a gearing ratio of 1:1 which means that the axial movement of the dose selector 4 during injection is equal to the axial movement of the piston rod 8 and the piston 40. In addition the dose selector 4 moves a little distance to engage/disengage from the driver 6 in the teeth connection 17/28 and to cause scale drum 5 and the ratchet 7 to engage in the teeth connection 24/30.

Figure 3:
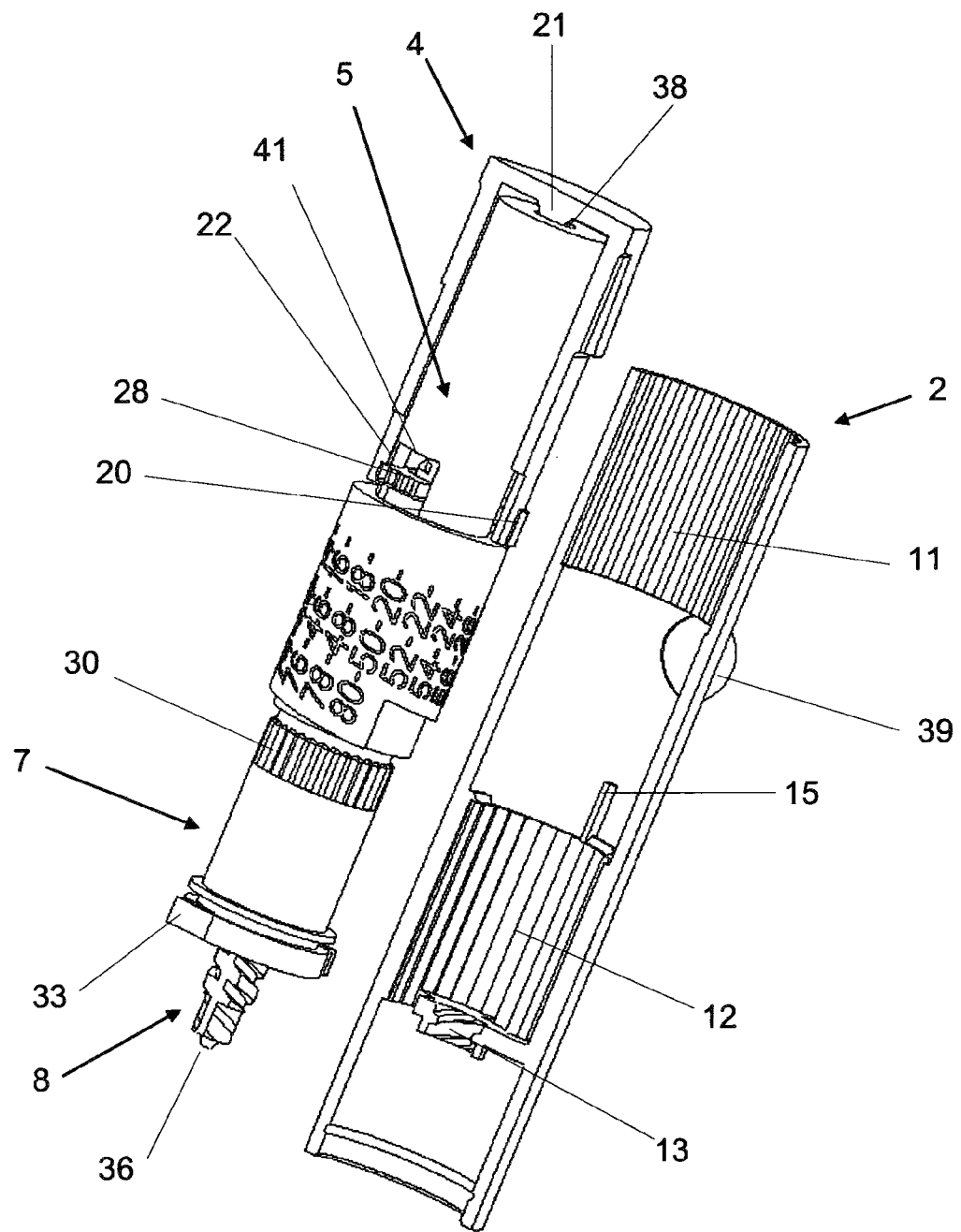
FIG. 3 shows a partly exploded view of the dose setting mechanism of a device according to the invention, FIG. 4 schematically shows a vertical sectional view of a device according to the invention ready to set a dose, FIG. 5 schematically shows a vertical sectional view of a device according to the invention where a dose has been set, FIG. 6 schematically shows a vertical sectional view of a device according to the invention where the dose setting member has been pushed and the driver is disengaged, FIG. 7 schematically shows a vertical sectional view of a device according to the invention where a dose has been injected but the dose setting member is still depressed, FIG. 8 schematically shows a vertical sectional view of an embodiment of a device according to the invention with an axial movable window where a dose has been set

The dose setting and the dose injection mechanisms are highly integrated and the change from dose setting mode to dose injection mode is due to an initial movement of the integrated push-button and dose selector 4 before the actual injection starts. The mechanism comprises the following moving parts: a dose selector 4, a piston rod 8, a ratchet 7, a driver 6, a scale drum 5, the dose selector 4 and these parts cooperates with the housing 2. The piston rod 8 has a thread 35 and is engaged with the housing 2 via a thread 13 in a narrowing and at the same time the piston rod 8 is engaged with a thread 26 on the driver 6. A unidirectional ratchet 7 is axial locked to the driver 6 and is rotational locked to the piston rod 8 via a key/groove connection and allows rotation of the piston rod 8 in only one direction due to the ratchet arms 33 which interacts with teeth 12 in the housing 2. A scale drum 5 displaying the amount of a set dose is rotational locked to the driver 6 and is capable of moving a small axial distance relative to the driver 6 which allows it to be rotational connected with the ratchet 7 due to teeth on both items 24/30 during injection. A dose selector 4 is mating the scale drum 5 via gliding surfaces 21/38 on the two items. The dose selector 4 is coupled to the driver 6 via sets of teeth 17/28 when a dose is set, and decoupled by a small initial axial movement when a dose is injected and to allow this connection, the scale drum 5 has a pair of openings 22 for the teeth 28 on the driver 6. The dose selector 4 furthermore comprises knobs 20 (visible on FIG. 3) on the outer surface which cooperates with grooves 11 in the housing 2 in such a way that they act as bidirectional ratchet which will index the dose selector 4 and thereby the driver 6 and the scale drum 5 in positions equally spaced around the main axis of the device, and the distance between two increments corresponding to a unit of the drug to be injected. This bidirectional ratchet also gives the user an audible and tactile feed-back which allows the user to count the units when setting a dose.

Between the driver 6 and the scale drum 5 a spring mechanism is provided. Two flexible arms 29 on the driver 6 are sliding over slanted ribs 27 in the scale drum 5 near the top. When the driver 6 and the scale drum 5 are pressed together, the flexible arms 29 will bend and act with a force on the slanted ribs 27 perpendicular to the axis of the device and along the axis of the device. The force along the axis of the device will try to take apart the parts as the flexible arms 29 try to straighten out and regain their original form. A flange 18 on the dose selector 4 mates the lower surface of the teeth segments 28 of the driver 6 and prevents the parts from going a part.

The housing 2 has an opening to allow the user to read a set dose and this opening is equipped with a window which is preferably formed as a magnifier to ease the readability of the set dose.

In the following all sequences related to having an injection are described with references to FIGS. 4-7.

Figure 4:
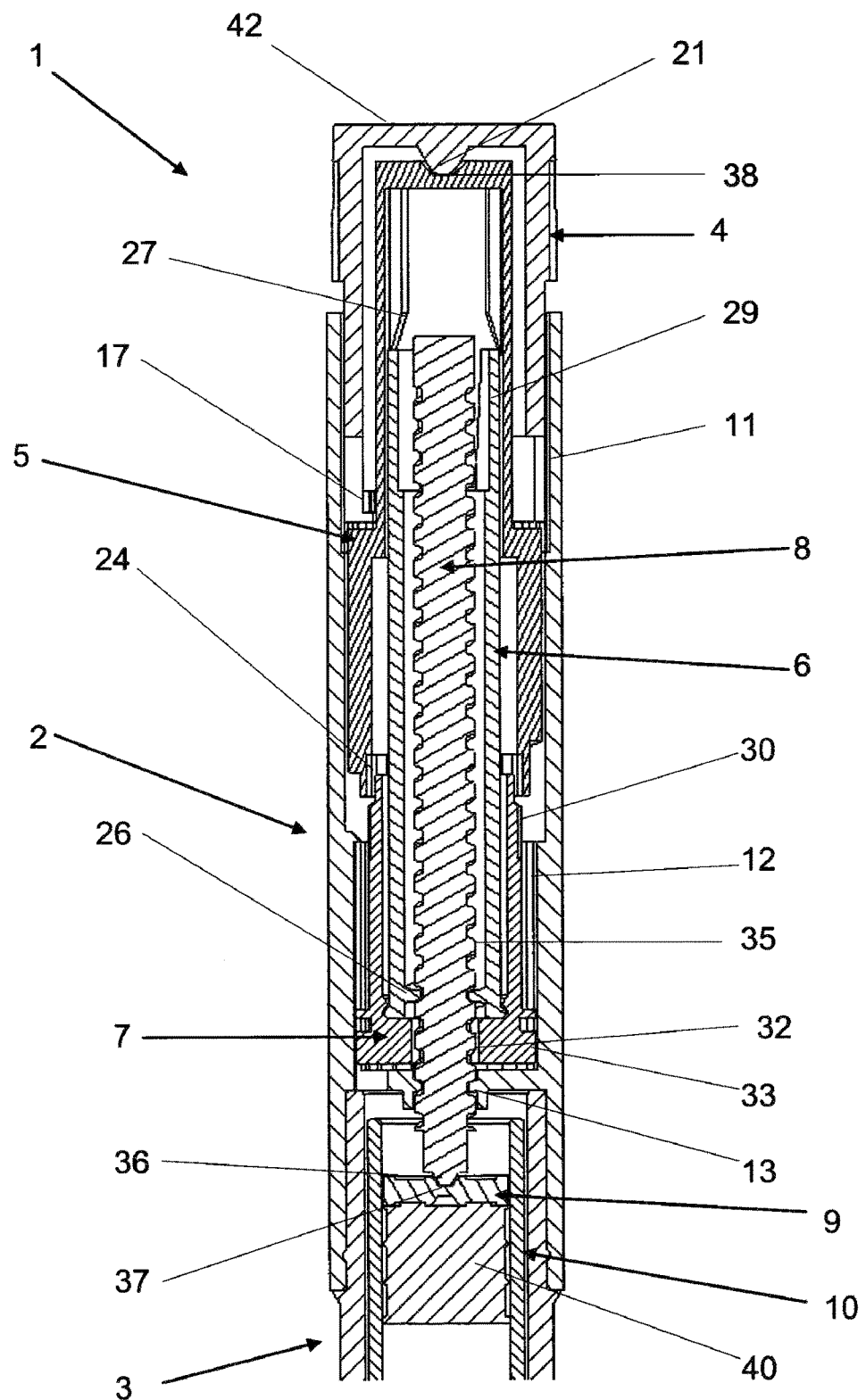

FIG. 4 shows a device 1 according to the invention ready to set a dose. As it can be seen the spring function 27/29 between the driver 6 and the scale drum 5 is in its relaxed position and the dose selector 4 and the scale drum 5 are in their non depressed position. Consequently the dose selector 4 is engaging the driver 6 via the teeth connection 17/28 and the scale drum 5 is decoupled 24/30 from the ratchet 7. The piston rod 8 is locked against rotation in the dose setting direction due to the ratchet arms 33 on the ratchet 7, and the rotational position of the scale drum 5 and the driver 6 is well defined due to thread engagement 26/35 between the driver 6 and the piston rod 8 and due to the rotational stop 15 in the housing 2 which cooperates with the stop surface 23 on the scale drum 5. The scale drum 5 displays 0 through the window 39 in the housing 2.

Figure 5:
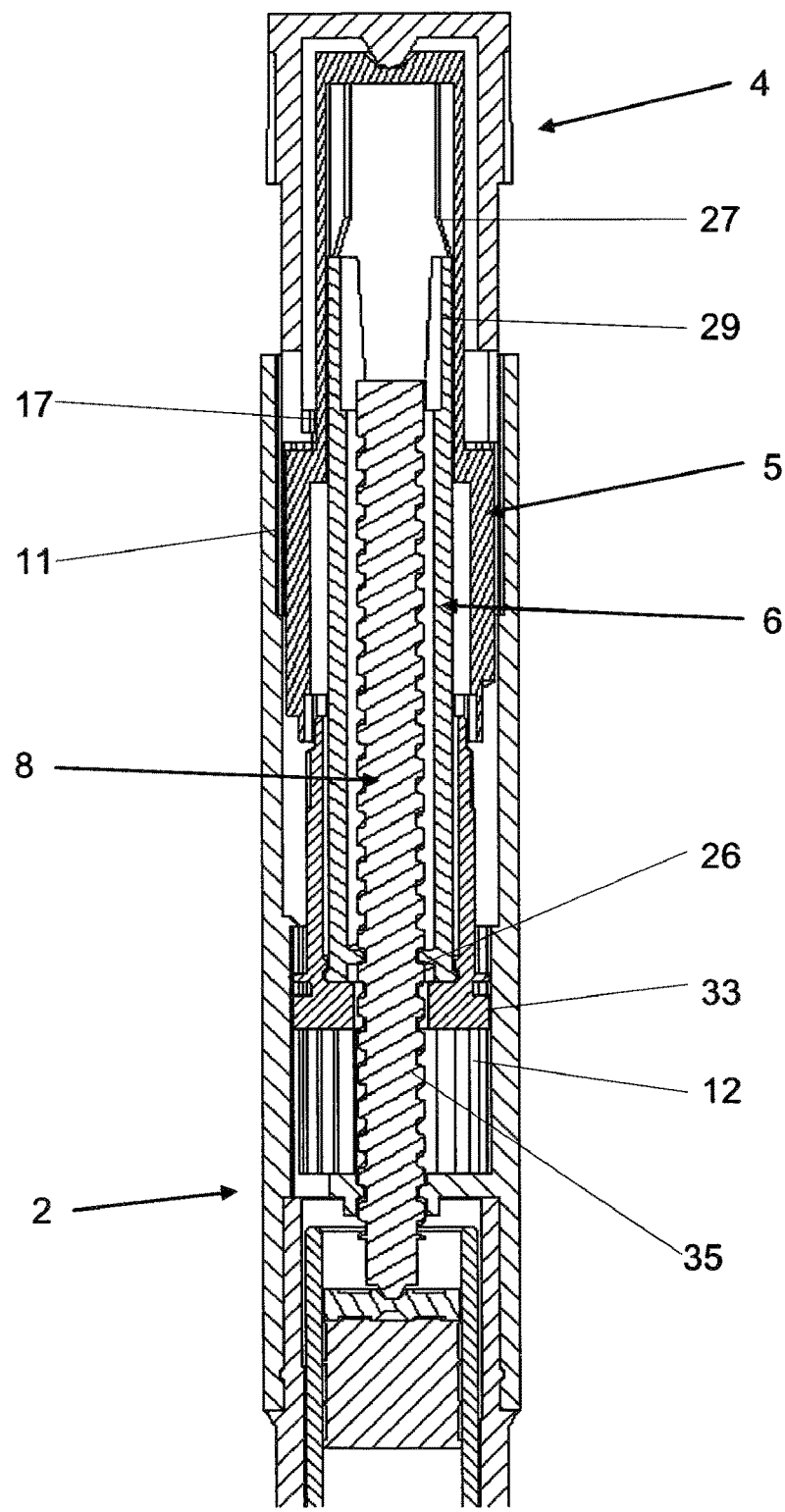

FIG. 5 shows a device 1 according to the invention where a dose has been set. To set the dose the dose selector 4 has been rotated clockwise which will cause it to produce a clicking and tactile feed-back due to the knobs 20 (see FIG. 3) on the outside of the dose selector 4 and the grooves 11 inside the housing 2. Due to the teeth engagement 17/28 between the dose selector 4 and the driver 6 the driver will be rotated as well and both items will at the same time elevate away from the needle end. The piston rod 8 is locked against rotation in the dose setting direction due to the ratchet arms 33 on the ratchet 7. The scale drum 5 will follow the driver 6 due to the spring connection 27/29 and the rotational connection formed by the cuts 22 in the scale drum 5 and the teeth sections 28 on the driver 6 and display the amount of the set dose through the window 39. If a dose has been wrongly set and consequently has to be corrected, the dose selector 4 is simply rotated anti-clockwise until the correct amount is displayed in the window 39. The rotational resistance in the ratchet 7 and the axial resistance between the piston 40 and the cartridge 10 will ensure that the piston rod 8 does not rotate during correction of the dose.

Figure 6:
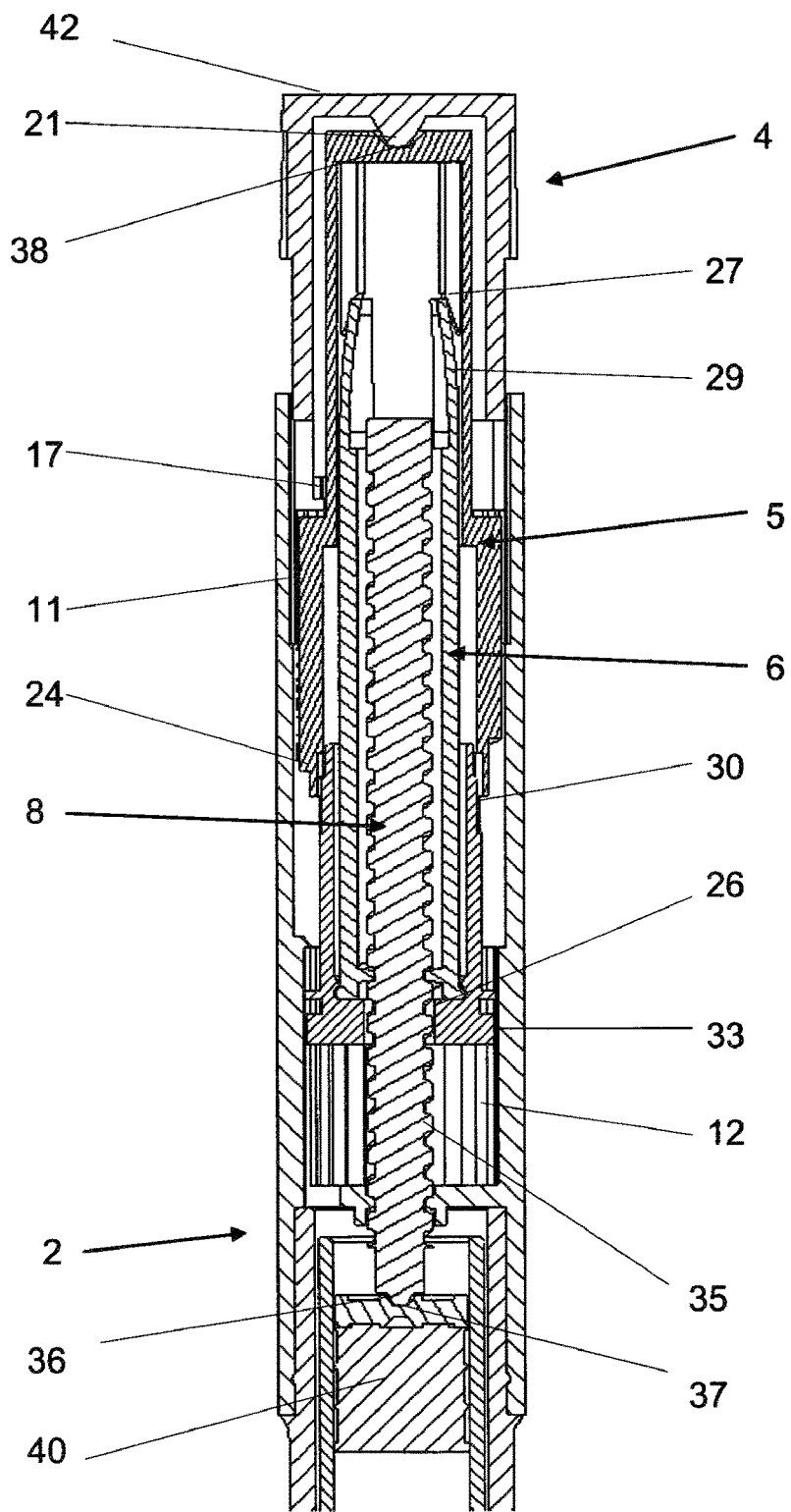

In FIG. 6 the dose selector 4 has been moved a small distance by a push on the upper surface 42 on the dose selector 4, just enough to decouple the teeth connection 17/28 (see FIG. 3) between the dose selector 4 and the driver 6 and to engage the teeth connection 24/30 between the scale drum 5 and the ratchet 7, but not enough to actually start the injection. It is clear that the flexible arms 29 on the driver 6 have been bent due to the interaction with the slanted surfaced 27 on the ribs inside the scale drum 5, and they now apply an axial force between the scale drum 5 and the driver 6, when they try to straighten out and gain there initial form. The piston rod 8, the driver 6, the scale drum 5 and the ratchet 7 are now coupled together and will move as one part as long as the dose selector 4 has been pushed. Because the surface 41 in the cut 22 in the scale drum 5 now mates the upper side of the teeth sections 28 on the driver 6 further push on the dose selector 4 will cause the piston rod 8, the driver 6, the scale drum 5 and the ratchet 7 to rotate causing a very little rotational resistance due to the gliding bearing 21/38 between the dose selector 4 and the scale drum 6 and the gliding bearing 36/37 between the piston rod 8 and the piston washer 9. They will now move axial toward the needle end due to the thread engagement 32/35 between the piston rod 8 and the housing 2, which again will move the piston 40 via the piston washer 9 and expel the medicament. Due to the disengagement from the driver 6 the dose selector 4 will not rotate due to further pushing, and any unintended rotation of the dose selector 4 during injection will not have any influence on the accuracy of the injected dose. During injection the ratchet arms 33 on the ratchet 7 will produce a clicking sound when jumping in and out in the grooves 12 in the housing 2.

Figure 7:
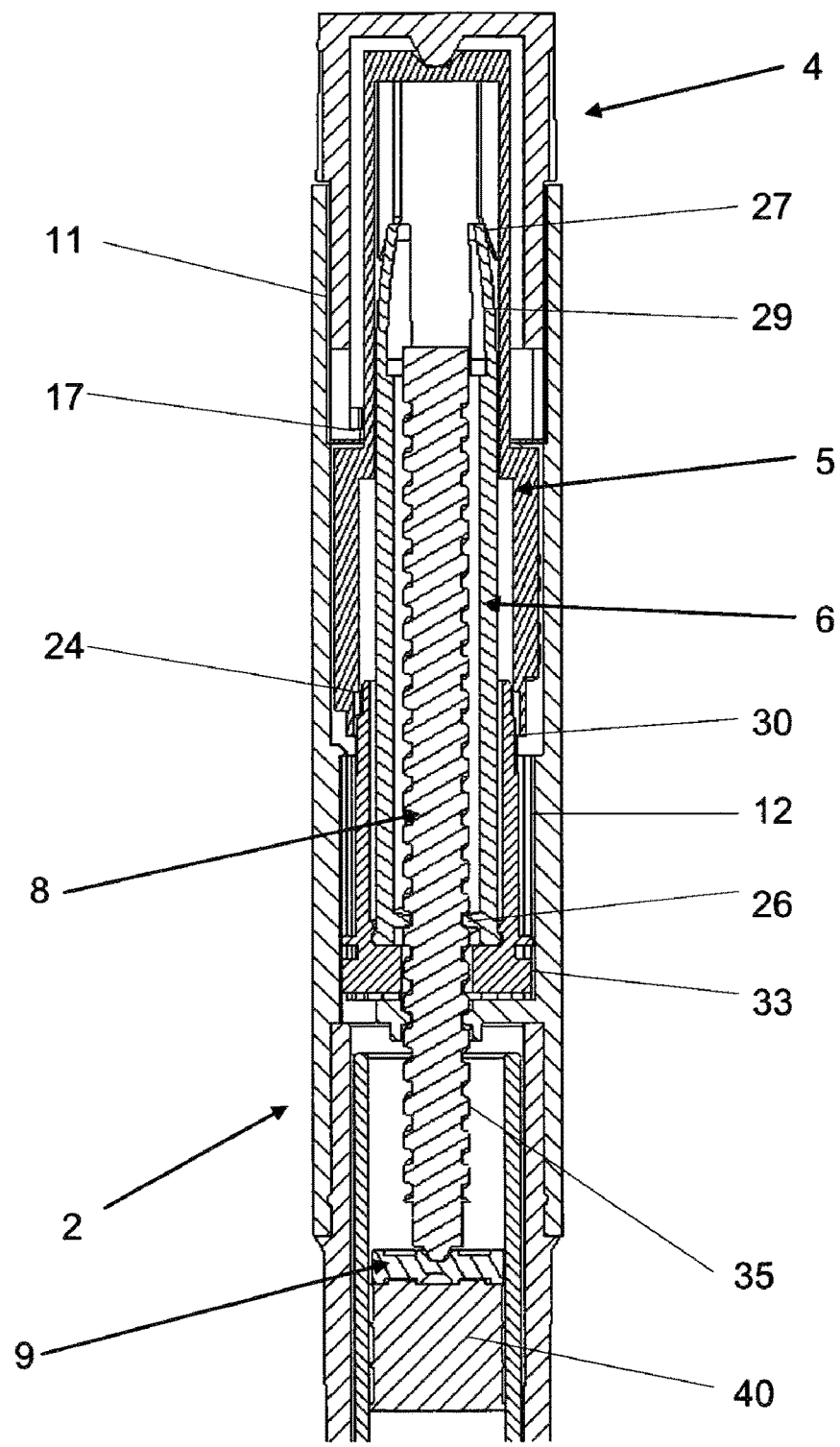

FIG. 7 shows a device according to the invention, where the injection of a set dose has just been accomplished and it is clear, that the piston rod 8, piston washer 9 and piston 40 has moved a distance corresponding to the amount of the set dose. The piston rod 8, the driver 6, the scale drum 5 and the ratchet 7 has all been rotated until the stop surface 23 on the scale drum 6 has mated the stop rib 15 in the housing 2 and the number "0" is displayed through the window 35 in the housing 2. The dose selector 4 is still depressed and to prepare the device for a new dose setting, the pressure on the dose selector 4 must be removed, which will engage the teeth connection 21/38 between the dose selector 4 and the driver 5 and decouple the teeth engagement 24/30 between the scale drum 5 and the ratchet 7 due to the spring function 27/29 between the driver 6 and the scale drum 5.

Figures 8, 9:
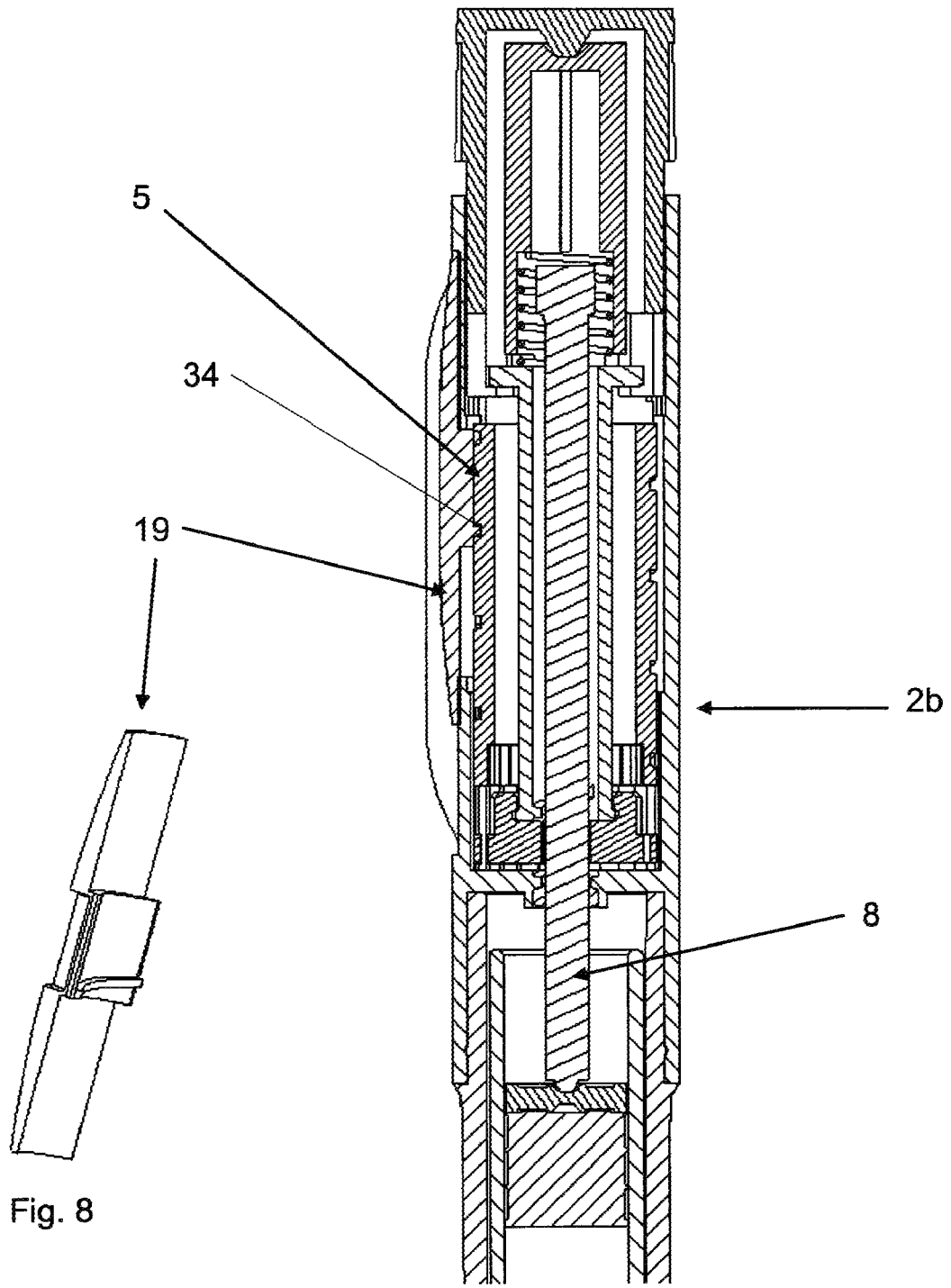
FIG. 9 shows a perspective view of the movable window according to the invention FIG. 10 schematically shows a vertical sectional view of an embodiment of a device according to the invention with an axial movable window where a dose has been set

FIG. 8 shows another embodiment of a device according to the invention. The scale drum 5b is provided with an outer thread 34 with a pitch which is handed the opposite way of the thread 35 on the piston rod 8. As the pitch of the thread 35 on the piston rod 8 is left handed, the pitch of the thread on the scale drum 5 is right handed. A sliding window 19 (see also FIG. 9) which is non rotational but axial movable in an elongated hole in the housing 2b has a thread segment which engages the thread 34 of the scale drum 5. The pitch of the thread 34 and the thread segment of the sliding window 19 should be higher than the pitch 35 of the piston rod 8 e.g. the double, so that the sliding window 19 will move towards the needle end, when the scale drum 5 moves away from the needle end. This makes it possible to provide the scale drum 5 with bigger numbers to ease the readability. The sliding window 19 can further form a magnifier to further increase the readability.

Figure 10:
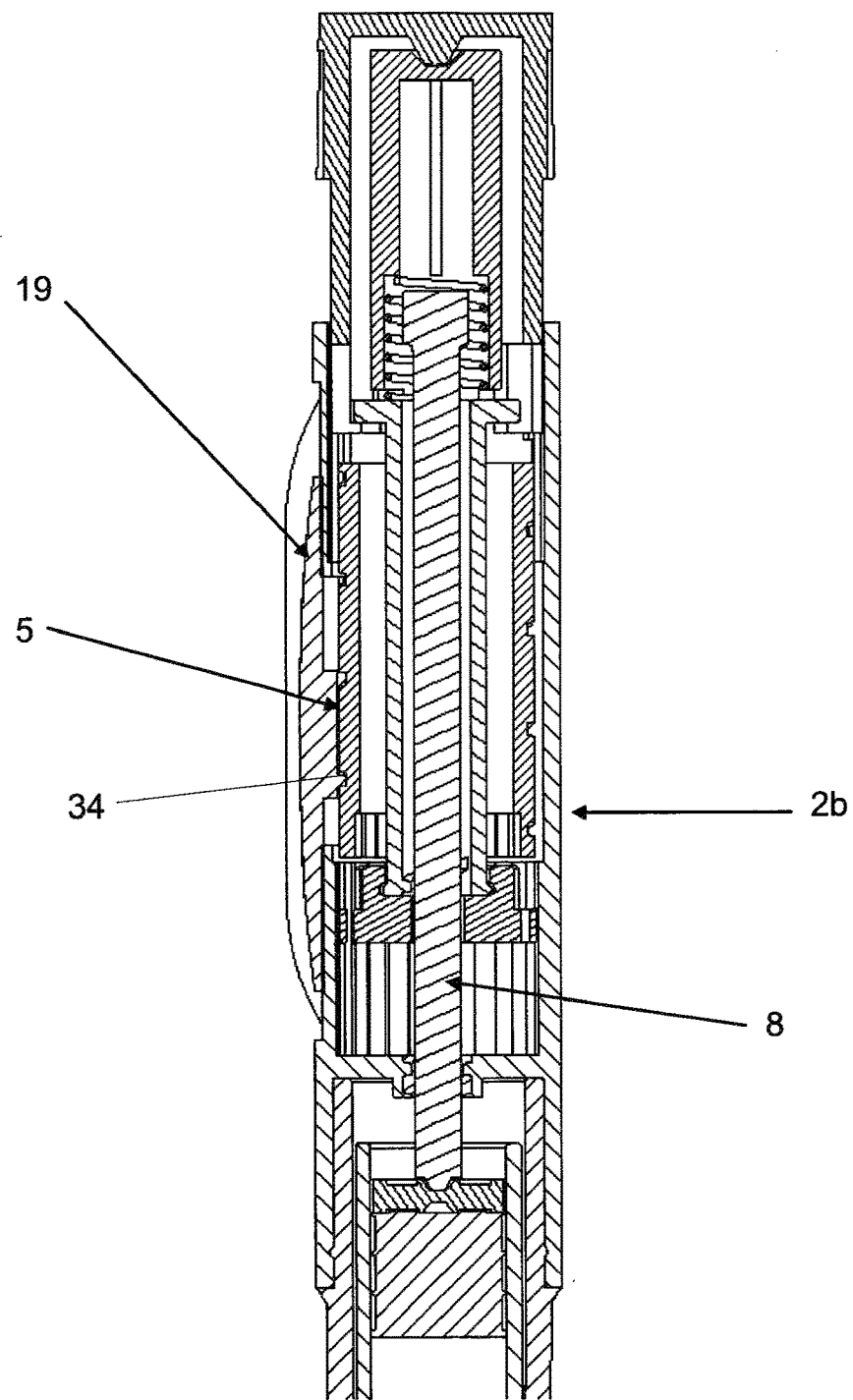

In FIG. 10 a dose has been set, and it is now obviously that the window 19 moves down when the scale drum 5 moves up, and that more space for numbers thereby is provided.

Figure 11:
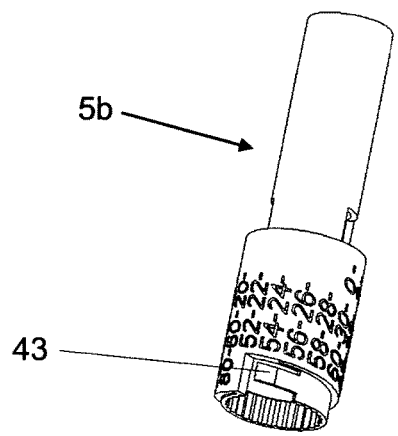
FIG. 11 shows a perspective view of the scale drum with an "end of dose" ratchet arm
Figure 12:
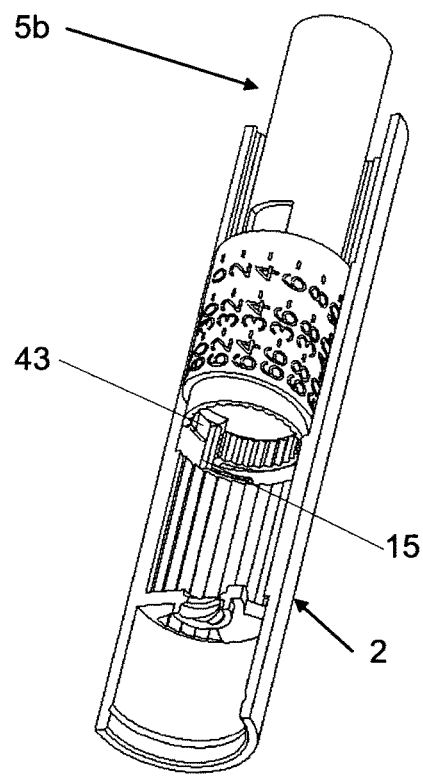
FIG. 12 shows a perspective view of the scale drum with an "end of dose" ratchet arm acting in the housing in a position where the push button is still depressed
Figure 13:
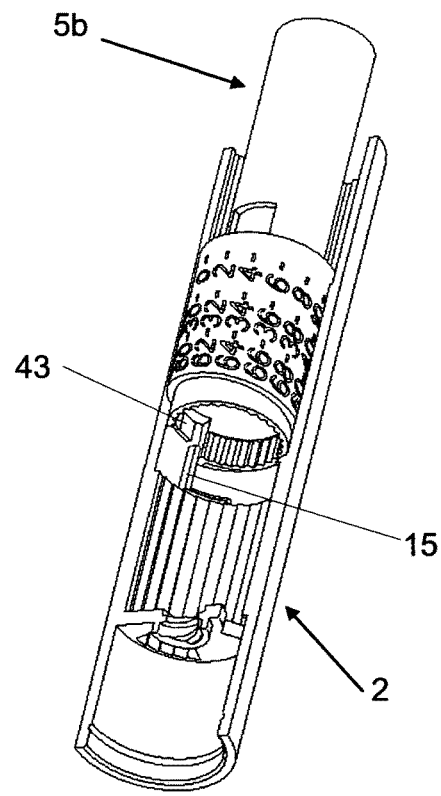
FIG. 13 shows a perspective view of the scale drum with an "end of dose" ratchet arm acting in the housing in a position where the push button is released

FIG. 11 shows a scale drum 5b with an "end of dose" ratchet arm 43 in a housing 2. When a dose is being injected, the ratchet is in an area where it is allowed to rotate freely, but in the end of the injection it has moved down to the level of the stop rib 15 and just before the injection stops, the "end of dose" ratchet arm will pass the stop rib 15 and this passage will cause the "end of dose" ratchet arm to be pushed and to fall down behind the stop rib 15 creating a clicking sound, which should be designed to be different from the sound of the injection clicks. When the pressure on the push-button is released, the "end of dose" ratchet arm 43 will move to a level relative to the stop rib 15 where it is capable of moving in the stop direction of the ratchet 43 and a new dose can be set.

The invention claimed is:

1. A dose delivery device comprising:
    a housing;
    a dose selector;
    a push-button;
    a piston rod threadably engaged to the housing, the piston rod not rotating during dose setting and rotating during injection;
    a driver threadedly engaged with the piston rod and having a flexible arm; and
    a numbered scale drum rotationally locked to the driver during dose setting and injection and axially moveable with respect to the driver, the scale drum having a slanted rib extending toward the driver;
    wherein when the driver and the scale drum are pressed together, axial movement of the scale drum toward the driver causes the slanted rib to engage the flexible arm and apply an axial force between the slanted rib of the scale drum and the flexible arm of the driver,
    wherein a dose can be set by rotating the dose selector, whereby the push-button is elevated from one end of the device a distance proportional to the set dose from a position fixed relative to the housing,
    wherein the set dose can be injected by pressing the push-button back to its non-elevated position, through which motion the piston rod and the driver will move the same distance, at least after an initial movement of the push-button, and
    wherein the driver follows a helical path in one direction when setting a dose and the driver follows the same helical path in an opposite direction and together with the piston rod when injecting the set dose.

2. A dose delivery device according to claim 1, wherein the dose selector and the push-button are formed as one integral part.

3. A dose delivery device according to claim 1, wherein the numbered scale drum displaying the amount of a set dose is axially locked to the push-button.

4. A dose delivery device according to claim 3, further comprising a stop surface on the numbered scale drum cooperating with a protrusion in the housing when a dose injection is completed.

5. A dose delivery device according to claim 3, further comprising a ratchet axially locked to the driver, and wherein the numbered scale drum couples rotationally to the ratchet when the push-button is pushed.

6. A dose delivery device according to claim 3, wherein a non-rotational window is axially movable and is engaged with the numbered scale drum via a thread in such a way, that it moves axially in the opposite direction of the driver when setting and injecting a dose.

7. A dose delivery device according to claim 6, further comprising a magnifier which enlarges a displayed number corresponding to the set dose.

8. A dose delivery device according to claim 1, wherein the numbered drum engages a first thread in the housing having a first pitch and a second thread on the driver having a second pitch, the second pitch being higher than the first pitch.

9. A dose delivery device according to claim 1, wherein the dose selector is rotationally coupled to the driver during dose setting and decoupled during injection.

10. A dose delivery device according to claim 1, wherein the dose selector is rotationally indexed on the housing about equal spaces around a center axis of the device, and wherein rotation of the dose selector produces audible and tactile feed-back due to an interaction between the dose selector and the housing.

11. A dose delivery device according to claim 1, wherein a ratchet is provided between the dose selector and the driver.

12. A dose delivery device according to claim 1, wherein a one-way ratchet is rotationally coupled to the piston rod and produces a clicking sound when injecting the dose.

13. A dose delivery device according to claim 1, wherein a ratchet is rotationally fixed to the housing during dose setting, rotatable with respect to the housing at least in one direction during injection, and rotationally coupled to the piston rod.

14. A dose delivery device comprising:
    a housing;
    a dose selector moveable in a proximal direction to set a dose;
    a driver rotationally coupled to the dose selector during dose setting, said driver having a flexible arm extending toward the dose selector;
    a scale drum rotationally locked to the driver during dose setting and injection and axially moveable with respect to the driver, said scale drum having a slanted rib extending toward the driver;
    a ratchet axially locked to the driver; and
    a piston rod threadably engaged to the housing, the piston rod rotationally locked to the ratchet,
    wherein when the driver and the scale drum are pressed together, axial movement of the scale drum toward the driver causes the slanted rib to engage the flexible arm and apply an axial force between the slanted rib of the scale drum and the flexible arm of the driver; and
    wherein the driver follows a helical path in one direction during dose setting and the driver follows the same helical path in an opposite direction when injecting the set dose.

15. The device of claim 14, wherein the ratchet comprises a ratchet arm preventing rotation of the piston during dose setting.

16. The device of claim 14, wherein the housing comprises a set of grooves and the dose selector comprises a knob engaging the grooves to index the rotational position of the dose selector during dose setting.

17. The device of claim 14, wherein the flexible arm extends axially from the driver.

18. The device of claim 14, wherein during dose setting, the dose selector is coupled to the driver and the scale drum is decoupled from the ratchet.

19. The device of claim 18, wherein during injecting the set dose, the dose selector is decoupled from the driver and the scale drum is coupled to the ratchet.

20. The device of claim 19, wherein the driver, scale drum, ratchet and piston rod are rotationally coupled and rotate with respect to the housing when injecting the set dose.

* * * * *